(12) United States Patent
Butler et al.

(10) Patent No.: US 9,561,332 B2
(45) Date of Patent: Feb. 7, 2017

(54) DECODING SYSTEM

(71) Applicant: SANOFI-AVENTIS DEUTSCHLAND GMBH, Frankfurt am Main (DE)

(72) Inventors: Joseph Butler, Warwickshire (GB); Paul Richard Draper, Worcestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/760,434

(22) PCT Filed: Jan. 13, 2014

(86) PCT No.: PCT/EP2014/050468
§ 371 (c)(1),
(2) Date: Jul. 10, 2015

(87) PCT Pub. No.: WO2014/111341
PCT Pub. Date: Jul. 24, 2014

(65) Prior Publication Data
US 2015/0343152 A1    Dec. 3, 2015

(30) Foreign Application Priority Data

Jan. 15, 2013 (EP) ..................................... 13151371

(51) Int. Cl.
*G06F 17/00* (2006.01)
*A61M 5/315* (2006.01)
*A61M 5/24* (2006.01)

(52) U.S. Cl.
CPC ..... *A61M 5/31551* (2013.01); *A61M 5/31568* (2013.01); *A61M 5/31585* (2013.01); *A61M 5/24* (2013.01); *A61M 2205/52* (2013.01)

(58) Field of Classification Search
USPC ................................ 235/375, 462.01, 462.09
See application file for complete search history.

(56) References Cited

U.S. PATENT DOCUMENTS 8,574,198 B2 * 11/2013 Veasey .................... A61M 5/24
604/207
9,192,728 B2 * 11/2015 Gilmore ............ A61M 5/31551
(Continued)

FOREIGN PATENT DOCUMENTS

WO    2006/045523    5/2006
WO    2010/052275    5/2010
(Continued)

OTHER PUBLICATIONS

International Search Report for Int. App. No. PCT/EP2014/050468, completed Mar. 25, 2014.
(Continued)

*Primary Examiner* — Ahshik Kim
(74) *Attorney, Agent, or Firm* — McDonnell Boehnen Hulbert & Berghoff LLP

(57) ABSTRACT

A decoding system for use with a drug delivery device having a drug dose dialing mode and a drug dose delivery mode is presented where the decoding system comprising has a first sensor configured to read encoded information from a first rotatable component of a drug delivery device, a second sensor configured to read encoded information from a second rotatable component of a drug delivery device, wherein the second sensor comprises an optical sensor configured to be directed at the second rotatable component, and a processor. The processor is configured to receive signals from the first and second sensors, and to determine from the received signals whether the drug delivery device is in a drug dose dialing mode or a drug dose delivery mode.

13 Claims, 4 Drawing Sheets

(56) References Cited

U.S. PATENT DOCUMENTS

| | | |
|---|---|---|
| 9,238,106 B2 * | 1/2016 | Jones .................. A61M 5/24 |
| 9,248,239 B2 * | 2/2016 | Leak .................. A61M 5/3155 |
| 2004/0207385 A1 | 10/2004 | Garner et al. |

FOREIGN PATENT DOCUMENTS

| | | |
|---|---|---|
| WO | 2010/139640 | 12/2010 |
| WO | 2011/117212 | 9/2011 |
| WO | 2012/140097 | 10/2012 |
| WO | 2013/004844 | 1/2013 |

OTHER PUBLICATIONS

European Search Report for EP App. No. 13151371, dated Jul. 18, 2013.

* cited by examiner

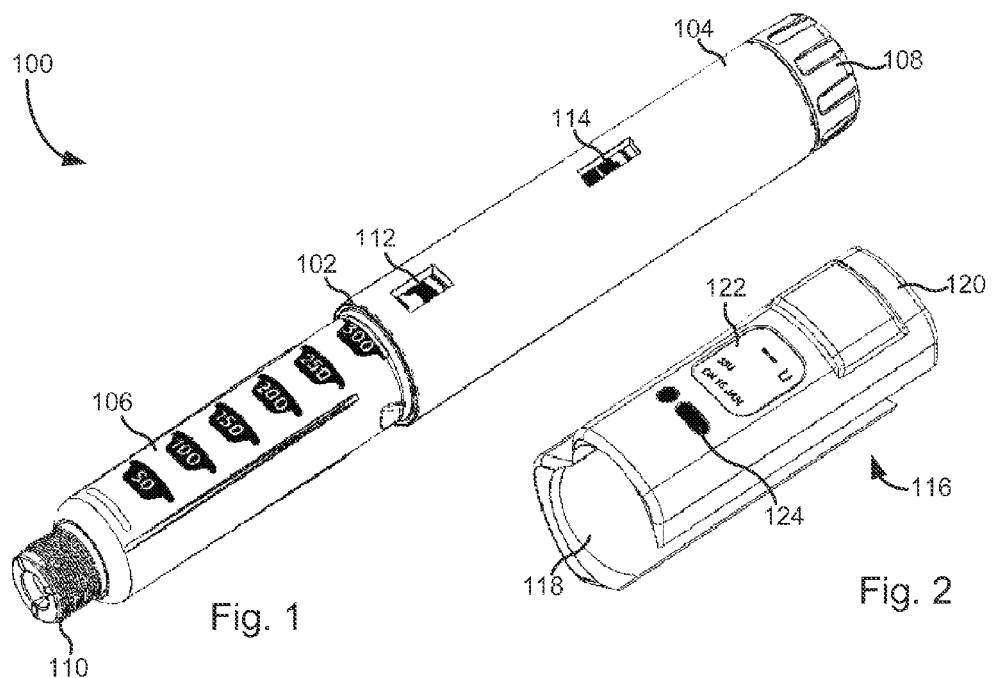
Fig. 1
Fig. 2
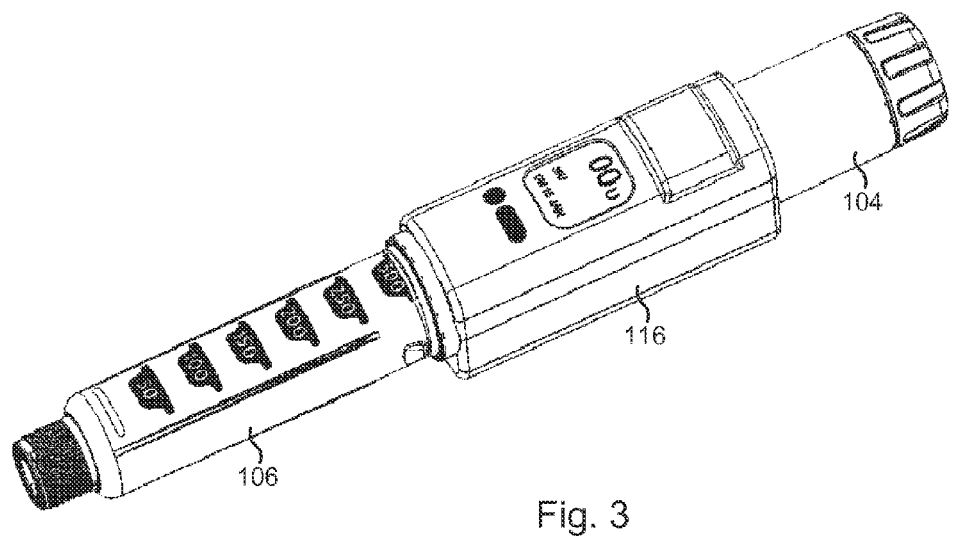
Fig. 3

DECODING SYSTEM

CROSS REFERENCE TO RELATED APPLICATIONS

The present application is a U.S. National Phase Application pursuant to 35 U.S.C. §371 of International Application No. PCT/EP2014/050468 filed Jan. 13, 2014, which claims priority to European Patent Application No. 13151371.5 filed Jan. 15, 2013. The entire disclosure contents of these applications are herewith incorporated by reference into the present application.

TECHNICAL FIELD

The present invention relates to a decoding system for a drug delivery device.

BACKGROUND

Pen type drug delivery devices have application where regular injection by persons without formal medical training occurs. This is increasingly common among patients having diabetes where self-treatment enables such patients to conduct effective management of their diabetes. For instance, a pre-filled disposable insulin pen can be used as an injection device. Alternatively, a re-usable pen may be used. A re-usable pen allows replacement of an empty medicament cartridge by a new one.

For good or perfect glycemic control, the dose of insulin or insulin glargine has to be adjusted for each individual in accordance with a blood glucose level to be achieved. The present invention relates to decoding systems for injectors, for example hand-held injectors, especially pen-type injectors, that is to injectors of the kind that provide for administration by injection of medicinal products from a multidose cartridge.

A user undertaking self-administration of insulin will commonly need to administer between 1 and 80 International Units. A user is also required to record their dosage history. The dosage history is an important factor in calculating future doses.

SUMMARY

A first aspect of the invention provides a decoding system for use with a drug delivery device having a drug dose dialing mode and a drug dose delivery mode, the decoding system comprising:

a first sensor configured to read encoded information from a first rotatable component of a drug delivery device;

a second sensor configured to read encoded information from a second rotatable component of a drug delivery device, wherein the second sensor comprises an optical sensor configured to be directed at the second rotatable component; and a processor configured to:

receive signals from the first and second sensors;

determine from the received signals whether the drug delivery device is in a drug dose dialing mode or a drug dose delivery mode.

The current mode of operation, e.g. a drug dose dialing mode or a drug dose delivery mode, of the drug delivery device can then be communicated to a user of the device. The user does not have to determine the mode themselves.

In an embodiment, the processor may be configured to determine, from signals received from the first sensor, a drug dose that has been delivered. This allows the delivered dose to be calculated automatically and accurately. It is often necessary for a user of such a drug delivery device to adjust the medicament dose based at least in part on their previous doses. It is therefore advantageous to accurately and automatically record all dispensed doses.

In another embodiment, the first sensor may comprise an optical sensor configured to be directed at the first rotatable component. The outer surface of the first rotatable component may be provided with a track comprising a sequence of encoded images and the optical sensor may be configured to be directed at the track so as to read the encoded images. The encoded images allow unique information to be encoded. Each encoded image may represent a unique rotational position of the first rotatable component. Alternatively, the sequence of observed encoded images may be used to determine the amount of rotation of the first rotatable component.

In another embodiment, the first sensor may comprise an array of one or more contacts configured to engage with the first rotatable component. An outer surface of the first rotatable component may be provided with a plurality of tracks together forming an encoder, each track comprising conductive segments and non-conductive segments, and each track may be configured to be engaged by at least one of the one or more contacts. The encoder formed by the tracks may encode a series of unique rotational positions of the first rotatable component.

The second sensor comprises an optical sensor configured to be directed at the second rotatable component. An outer surface of the second rotatable component may be provided with a track comprising a sequence of encoded images and the optical sensor may be configured to be directed at the track so as to read the encoded images. The encoded images allow unique information to be encoded. Each encoded image may represent a unique rotational position of the second rotatable component. Alternatively, the sequence of observed encoded images may be used to determine the amount of rotation of the second rotatable component.

In another embodiment, the second sensor may comprise an array of one or more contacts configured to engage with the second rotatable component. An outer surface of the second rotatable component may be provided with at least one track forming an encoder, each track comprising conductive segments and non-conductive segments, and each track may be configured to be engaged by at least one of the one or more contacts.

In another embodiment, the processor may be further configured to determine, from signals received from the second sensor, a drug dose that has been dialed into the drug delivery device. This allows the dialed dose to be automatically and accurately determined.

The first rotatable component may be arranged not to rotate relative to the first sensor when the drug delivery device is in a first mode and to rotate relative to the first sensor when the drug delivery device is a second mode; and the second rotatable component may be arranged to rotate and translate relative to the second sensor when the drug delivery device is in a first mode and in a second mode. The difference in movement between the first and second rotatable components allows the operational mode of the device to be determined.

The first mode may be a drug dose dialing mode and the second mode may be a drug dose delivery mode.

One of the advantages of using an optical sensor, rather than conductive contacts, is that conductive contacts result in mechanical friction which can affect the ease of use of the drug delivery device by increasing the force required to dial in and dispense a dose.

The present invention could be embodied in a re-usable drug delivery device, rather than a single use disposable device, and so mechanical wear may also become a problem and could decrease the long term reliability of the dose detection process.

Where the invention is embodied in a separate device configured to be attached to a drug delivery device, be it a re-usable or disposable drug delivery device, having an optical sensor is also advantageous as a mechanical connection between separate (user assembled) components is not required and no access aperture is required. Instead, a transparent window, e.g., is sufficient to direct an optical sensor at a rotatable component.

A second aspect of the invention provides a drug delivery device comprising a housing retaining the decoding system of the first aspect of the invention. The drug delivery device may comprise the first rotatable component the second rotatable component. Integrating the decoding system with the drug delivery device increases the utility of that device.

In a third aspect of the invention, the decoding system may be part of a supplementary device configured to be attached to the drug delivery device. Implementing the decoding system in a supplementary device allows the decoding system to be applied to devices without an electronic monitoring capability, or with a less sophisticated monitoring capability.

A fourth aspect of the invention provides a method of using a decoding system comprising:

receiving a signal from a first sensor configured to read encoded information from a first rotatable component of a drug delivery device;

receiving a signal from a second sensor configured to read encoded information from a second rotatable component of a drug delivery device; and determining that the drug delivery device is in a first mode of operation if there is a change detected in the readings from the second rotatable component and no change detected in the readings from the first rotatable component, or determining that the drug delivery device is in a second mode of operation if there is a change detected in the readings from the first and second rotatable components.

BRIEF DESCRIPTION OF THE DRAWINGS

Embodiments will now be described, by way of example only, with reference to the accompanying drawings, in which:

FIG. 1 shows an external view of a drug delivery device suitable for use in the present invention;

FIG. 2 shows a supplementary device according to embodiments of the invention;

FIG. 3 shows the supplementary device of FIG. 2 attached to the drug delivery device of FIG. 1;

DETAILED DESCRIPTION

Figure 4:
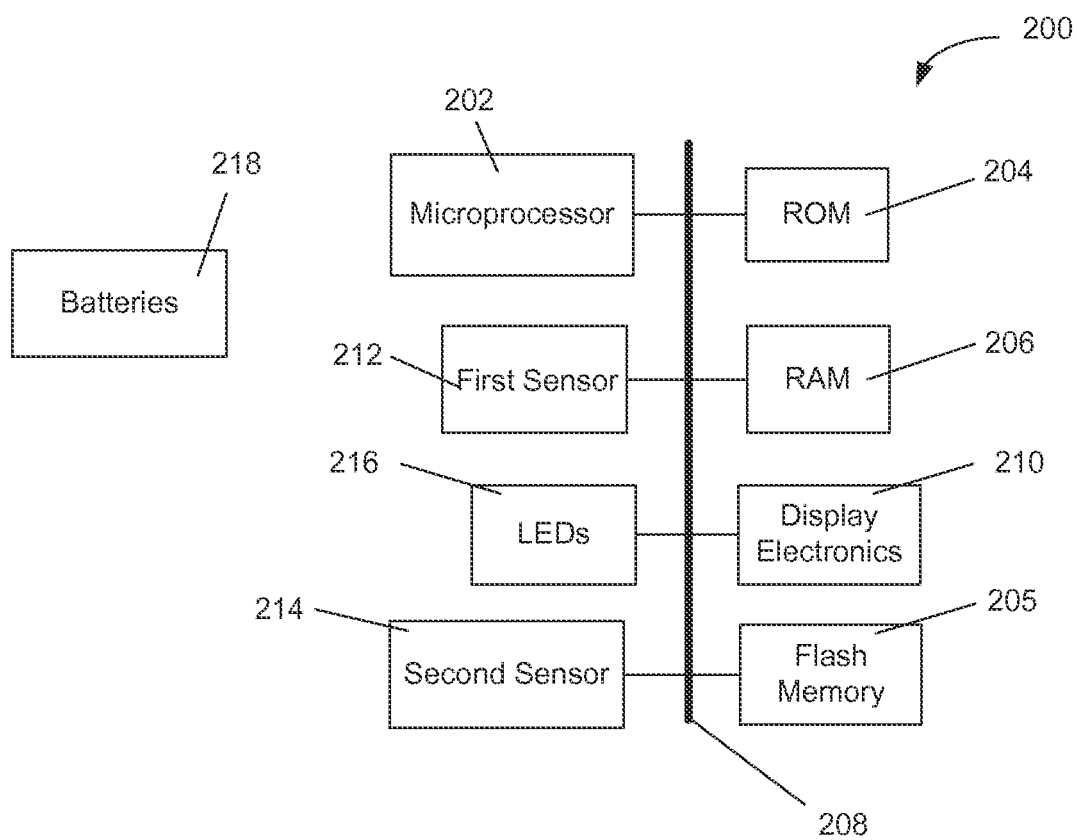
FIG. 4 shows a schematic diagram of some of the electronic components suitable for implementing the present invention.

Referring firstly to FIG. 1, an external view of a drug delivery device 100 suitable for use in the present invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A first aperture 112 is located in the first housing part 104, towards the distal end of the first housing part. In some embodiments, the first aperture 112 is a window providing access to the drug device mechanism housed within the first housing part 104. In some other embodiments, a transparent cover is disposed in the first aperture 112, which allows the mechanism housed within the first housing part 104 to be viewed. A second aperture 114 is located in the first housing part 104. The second aperture 114 is located closer to the proximal end of the first housing part 104 than the first aperture 112. The second aperture 114 may be located approximately centrally in the first housing part 104. In some embodiments, the second aperture 114 is a window providing access to the drug device mechanism housed within the first housing part 104. In some other embodiments, a transparent cover is disposed in the second aperture 114, which allows the mechanism housed within the first housing part 104 to be viewed.

The second aperture 114 is shown extending longitudinally in the first housing part 104. However, the second aperture 114 may instead extend circumferentially or helically in the first housing part 104. The first and second apertures 112, 114 may be configured to receive modular inserts containing electronic components. These inserts may be installed during manufacture of the drug delivery device 100 such that they for, or appear to form, a part of the housing 102 of the device 100.

The first housing part 104 may comprise other components which are not shown in FIG. 1. For example the first housing part 104 may support a display and one or more user inputs. The display may be an LCD display, an e-ink display, a segmented display or any other suitable type of display. An e-ink display may be particularly suitable for a battery powered device as it is able to display the last image (for example the time/date and amount of the last dose administered) with zero power consumption. The user inputs may be buttons, keys or touch sensitive areas.

The first housing part 104 contains a drug dose setting and delivery mechanism. The second housing part 106 contains a drug cartridge (not visible in FIG. 1). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together is such a way as the drug cartridge is permanently contained with the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 is connected to an internal threading system which causes the dial 108 to be displaced axially from the housing 102 as it is rotated in a first direction. The device 100 is configured, once a drug dose has been set by rotation of the rotatable dial 108, to deliver the set drug dose when a user exerts an axial force at the proximal end of the device. In some injection pen devices, the rotatable dial 108 may support a button (not shown) which must be depressed in order to deliver the set drug dose.

FIG. 2 is an illustration of an embodiment of a supplementary device 116 configured to be releasably attached to the drug delivery device 100 of FIG. 1. The supplementary device 116 comprises a housing comprising a lower part 118 and an upper part 120. Both the lower part 118 and upper part 120 have substantially hollow half cylindrical constructions. The lower part 118 and upper part 120 are hinged together along one longitudinal edge. The second longitudinal edges of the lower part 118 and upper part 120 engage when the hinge is closed. When the hinge is opened, the supplementary device 116 can be fitted around the drug delivery device 100. Fastening means, such as a clip (not shown), may be provided on the second longitudinal edges of the lower part 118 and upper part 120, allowing the supplementary device 116 to be releasably secured to the drug delivery device 100.

The supplementary device 116 also comprises a display 122 and at least one user input 124. The display 122 may be an LCD display, an e-ink display, a segmented display or any other suitable type of display. The display 122 may be configured to display information such as drug dose measurements and menu screens. The display electronics 210 may also show additional information, such as the actual time, the time of the last usage/injection, a remaining battery capacity, one or more warning signs, and/or the like. The at least one user input 124 may take the form of a push button or touch sensitive area.

FIG. 2 represents only one possible construction of the supplementary device 116. In some other embodiments, the supplementary device 116 may have a partial cylindrical construction, for example comprising only the upper part 120 of the housing, and a mating unit configured and embrace the first housing part 104 of the drug delivery device 100. The mating unit may comprise two or more arm like extensions which engage with recesses in the first housing part 104 to secure the supplementary device 116 to the drug delivery device 100.

FIG. 3 shows the supplementary device 116 secured to the drug delivery device 100. The supplementary device 116 may comprise sensors disposed on the underside of the upper housing part 120 (and described in greater detail with respect to FIG. 4), which view or contact the parts of the drug delivery device mechanism housed in the first housing part 104. These sensors allow measurements of drug doses which are dialed into and dispensed from the drug delivery device 100.

Referring now to FIG. 4, a schematic diagram of electrical circuitry 200 suitable for implementing the present invention is shown. The circuitry 200 comprises a microprocessor 202, a non-volatile memory such as a ROM 204, a writable non-volatile memory such as flash memory 205, a volatile memory such as a RAM 206, display electronics 210, a first sensor 212, a second sensor 214, optional LEDs 216 and a bus 208 connecting each of these components. The circuitry 200 also comprises batteries 218 or some other suitable source of power for providing power to each of the components.

The circuitry 200 may be integral with the device 100. Alternatively, the circuitry 200 may be contained within the supplementary device 116. In addition, the circuitry 200 may comprise additional sensors, such as an optical character recognition (OCR) system or acoustical sensors.

The ROM 204 may be configured to store software and/or firmware. This software/firmware may control operations of the microprocessor 202. The microprocessor 202 utilises RAM 206 to execute the software/firmware stored in the ROM to control operation of the display electronics 210. As such the microprocessor 202 may also comprise a display driver. The processor 202 utilises the flash memory 205 to store determined amounts of dose dialed and/or determined amounts of dose dispensed, as will be described in more detail below. The display electronics 210 may correspond to the display 120 of the supplementary device 116.

The batteries 218 may provide power for each of the components including the first and second sensors 212, 214 and LEDs 216 (if present). The supply of power to the first and second sensors 212, 214 and LEDs 216 may be controlled by the microprocessor 202. The microprocessor 202 may receive signals from the first and second sensors 212, 214 and is configured to interpret these signals. Information may be provided to the display electronics 210 at suitable times by operation of the software/firmware and the microprocessor 202. This information may include measurements determined from the signals received by the microprocessor 202 from the first and second sensors 212, 214 such as the drug dose which has been set and/or delivered. The display electronics 210 may also be configured to display additional information, such as the actual time, the time of the last usage/injection, a remaining battery capacity, one or more warning signs, and/or the like.

In some embodiments, the first and second sensors 212, 214 each comprise an array of electrically conductive contacts and are also referred to herein as first contacts and second contacts. These contacts are arranged so as to engage with one or more tracks disposed on rotatable components of the mechanism of the drug delivery device 100. The first contacts may engage a first rotatable component and the second contacts may engage a second, different rotatable component. The microprocessor 202 may control the supply of electricity to the contacts. The microprocessor 202 may address each contact in the contact arrays separately and is able to receive signals from the contacts and thereby determine when the contacts are energised.

In some other embodiments of the invention, the first and second sensors 212, 214 are optical sensors and are also referred to herein as first optical sensor and second optical sensor. The first and second optical sensors are configured to be directed at rotatable components of the mechanism of the drug delivery device 100. The first optical sensor may be directed at a first rotatable component and the second optical sensor may be directed at a second rotatable component. Each optical sensor may be configured to capture pixelated greyscale images of images or patterns printed on the rotatable components. The printed images or patterns may optically encode information. The microprocessor 202 is configured to receive the captured images from the optical sensors and decode the encoded information.

The selection of either contact sensors or optical sensors for the first and second sensors 212, 214 depends on design factors such as any increase in friction causes by contact type sensors and the increased power requirements of optical sensors and their associated LEDs. Furthermore, the use of optical sensors may also be accompanied by the use of additional switches configured to activate the optical sensors and LEDs only when a movement of the rotatable components occurs. In general, the power drain of the conductive system is negligible while the drug delivery device 100 is not in use. The first and second sensors 212, 214 need not be of the same type, for example the first sensor 212 may be an optical sensor while the second sensor 214 is an array of contacts.

The one or more LEDs 216 may be used in these embodiments and are also directed at the printed images/patterns in order to provide illumination for the optical sensors. For example, the first and second optical sensors may detect the intensity pattern of light reflected from the printed images/patterns. The LEDs 216 and optical sensors may be configured to operate at various wavelengths of light. The LEDs 216 and sensors may, for example, operate in infra-red. Each of the first and second optical sensors may have an integral LED 216, or the LEDs 216 and sensors may comprise separate units. Software stored in the ROM 204 allows the microprocessor 202 to determine from the signals received from the first and second optical sensors whether each of the first and second rotatable components is rotating.

The circuitry 200 may comprise further components which are not shown. For example, the circuitry 200 may comprise one or more user inputs in the form of hardware or software keys. The circuitry 200 may comprise a speaker and/or a microphone. The circuitry 200 may also comprise one or more means of removing or communicating information stored in the ROM 204 or flash memory 205, such as a wireless transceiver, a card slot or a cable port (e.g. a USB port).

The circuitry 200 may form a part of the supplementary device 116. The first and second sensors 212, 214 and the LEDs 216 (if present) may be supported on the underside of the upper part 120 of the housing of the supplementary device 116.

In embodiments where the first and second sensors 212, 214 are arrays of contacts, the contacts protrude from the underside of the housing of the supplementary device 116 so as to pass through the first and second apertures 112, 114 when the supplementary device 116 is secured to the drug delivery device 100. The contacts may be sprung contacts biased away from the underside of the housing of the supplementary device 116 so that a good connection is made with the rotatable components of the drug delivery device 100. Alternatively, they may be flexible brush type contacts.

In embodiments where the first and second sensors 212, 214 are optical sensors, the optical sensors are arranged so as to view the area directly below the underside of the upper part 120 of the housing of the supplementary device 116. When the supplementary device 116 is secured to the drug delivery device 100, the first optical sensor is positioned directly over the first aperture 112 and the second optical sensor is positioned directly over the second aperture 114. In these embodiments, the first and second apertures 112, 114 may have transparent covers. Therefore, when the supplementary device 116 is secured to the drug delivery device 100, the first and second optical sensors are able to view the rotatable components of the drug delivery device 100.

Alternatively, the circuitry 200 may form part of the drug delivery device 100. In these embodiments, the supplementary device 116 is not required. A modular insert containing at least the first sensor 212 may be received in the first aperture 112. A modular insert containing at least the second sensor 214 may be received in the second aperture 114. One of these inserts may also contain the other components of the circuitry 200. Alternatively, the other components may be supported elsewhere in the drug delivery device 100. Conductive tracks may be disposed inside the first housing part 104, or on an internal surface of the first housing part 104 to link the first and second sensors 212, 214 to the other electronic components.

Figure 5A:
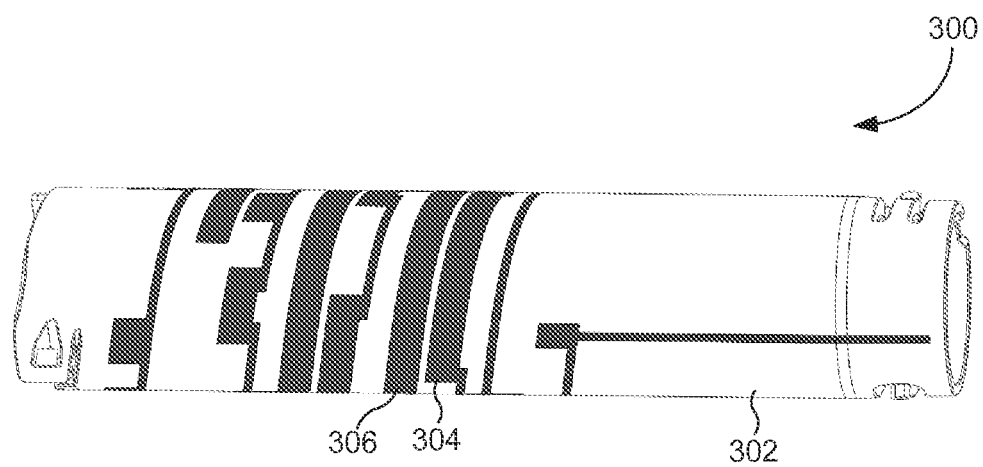
FIG. 5*a* shows an exemplary encoded number sleeve forming part of the drug delivery device of FIG. 1.
Figure 5B:
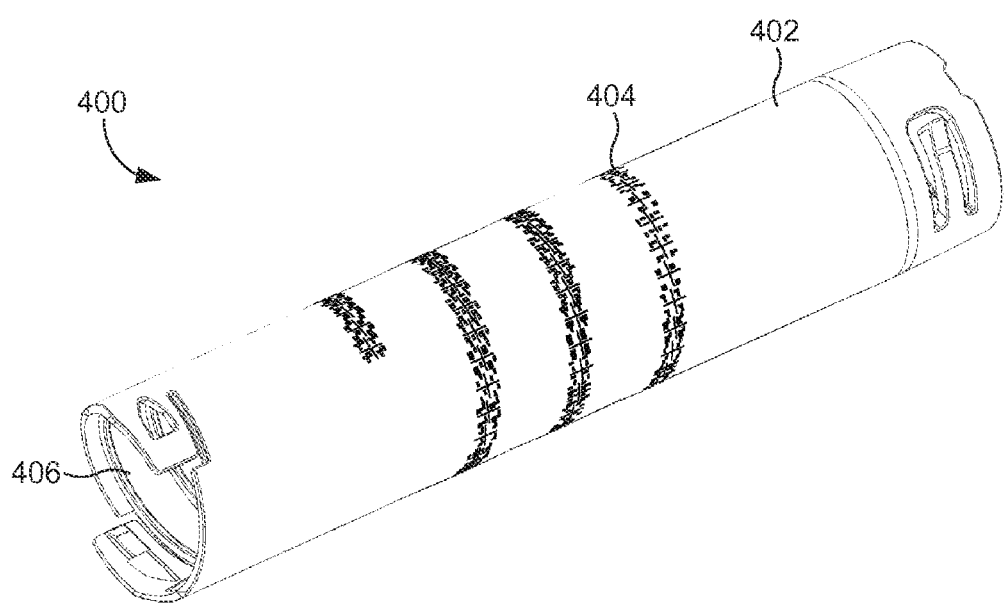
FIG. 5*b* shows an exemplary encoded number sleeve forming part of the drug delivery device of FIG. 1.

Referring now to FIGS. 5a and 5b, two examples of an encoded number sleeve are shown. These encoded number sleeves are the second rotatable component previously mentioned. FIG. 5a shows a plan view of a conductively encoded number sleeve 300 which forms part of the drug dose setting and delivery mechanism internal to the first housing part 104. FIG. 5b shows a perspective view of an optically encoded number sleeve 400 which forms part of the drug dose setting and delivery mechanism internal to the first housing part 104.

A detailed example of the operation of a dose setting and delivery mechanism can be found in published PCT application WO2010/139640, which is incorporated herein by reference. This document gives details of one particular drug delivery device mechanism. However, the invention may be implemented in a wide variety of different drug delivery devices having different mechanisms.

The conductively encoded number sleeve 300 is a hollow cylinder. An outer surface 302 of the encoded sleeve 300 comprises a first helical track 304 and a second helical track 306 arranged adjacent to one another. Each of the first and second tracks 304, 306 comprises conductive and non-conductive segments. In FIG. 5, the conductive segments are shown in black and the non-conductive segments are shown in white. In some embodiments, each of the first and second tracks 304, 306 comprises a measurement track and a ground or power track immediately adjacent to the measurement track. The effect of the ground track is to maintain an electrical connection between all of the conductive segments of each track.

The helical tracks 304, 306 on the outer surface 302 of the sleeve 300 may be formed by wrapping one or more metallic strips around the sleeve 300. The metallic strip may have a non-conductive backing to support the metallic layer. The non-conductive backing may have an adhesive on the reverse side for securing the strip to the outer surface 302 of the sleeve 300. The first and second helical tracks 304, 306 may be separated by a non-conductive strip. In some other embodiments, the tracks 304, 306 may comprise conductive ink printed onto a non-conductive substrate. This non-conductive substrate may be the sleeve 300 itself or a secondary substrate which is subsequently attached to the sleeve 300.

In some other embodiments, the outer surface 302 may have only one track comprising conductive and non-conductive segments and an adjacent power track. In some further embodiments, the outer surface 302 may have more than two tracks. For example, up to seven tracks may be provided, each track comprising conductive and non-conductive segments. The conductive and non-conductive segments of these tracks may be so arranged that all of the conductive segments are electrically connected, eliminating the need for a power track.

Each of the helical tracks is configured to be engaged by a number of contacts, which together form the second sensor 214. The contacts may be biased against the outer surface 302 of the encoded sleeve 300 in order to provide a stable electrical connection. The contacts may be spaced along the length of their respective track 304, 306. In some embodiments, the first track 304 is engaged by five contacts and the second track 306 is engaged by two contacts. However a different ratio may be used, for example 4:3. In some other embodiments, only one helical track is provided on the encoded number sleeve 300. This track may be engaged by all of the contacts forming the second sensor 214 at intervals along the length of the track. In some further embodiments, up to seven adjacent helical tracks are provided on the encoded number sleeve 300 and each track is engaged by a single contact. In order to accommodate the positions of the contacts, the second aperture 114 in the first housing part 104 may have a different shape to that shown in FIG. 1 and/or may be comprised of two or more separate apertures.

The microprocessor 202 may be configured to address each of the contacts individually. The microprocessor 202 is also configured to control the flow of electricity from the batteries 218 to each contact. However, when the batteries 218 provide a signal having a voltage to one of the contacts, certain others of the contacts may also be energized by virtue of being in electrical connection with the first contact via the conductive segments of the helical tracks. Thus, the batteries may provide a voltage to a first of the contacts (for example) and the microprocessor 202 may detect signals from each of the contacts which are energized by their electrical connection to the first contact. Since the microprocessor 202 can address the contacts individually, it is able to apply a signal to different contacts in a sequence, each time monitoring signals from the other contacts.

In the embodiment shown in FIG. 5*a*, the conductive and non-conductive segments of the helical tracks 304, 306 may be arranged in a repeating sequence. As the contacts are spaced along the tracks 304, 306, each contact sees a shifted version of the same sequence of code. In one embodiment, seven adjacent helical tracks are provided, each contacted by one of seven adjacent contacts. Each contact may therefore see a unique code determined by the sequence of conductive and non-conductive segments on its respective track. Having seven contacts results in a seven bit encoding system. Seven bits allows for a maximum of $2^7=128$ unique positions to be encoded. Thus the full 0-80 unit dial-able dose for an injection device can be "absolutely encoded" with redundant positions available. Having fewer than seven contacts does not allow the full 0-80 unit dose range to be absolutely encoded, but the dialed dose may be incrementally determined or determined quasi-absolutely.

FIG. 5*b* shows an optically encoded number sleeve 400. An outer surface 402 of the number sleeve 400 has a helical track 404 comprising a sequence of images.

The helical track 404 is configured to be viewed by a number sleeve sensor, which forms the first sensor 212. Each of the images encodes information and the microprocessor 202 is configured to decode this information. The number sleeve sensor is an optical sensor and may be configured to capture pixelated greyscale images of the images or patterns printed on the number sleeve 400. An LED 216 is provided to illuminate the track 404.

The drug delivery device 100 may be configured to deliver a maximum of 80 units of medicament. The track 404 may therefore comprise a series of 81 encoded images encoding positions 0 to 80. In some embodiments, the images are comprised of a number of data bits coloured black or white. The images may be repeated in the four quadrants of a square. This allows for the compensation of manufacturing tolerances which may prevent a single encoded image from being viewed fully by the number sleeve sensor. The images may each contain an orientating feature to allow the microprocessor 202 to determine the position of the image relative to the field of view of the number sleeve sensor. In some other embodiments, the encoded image scheme may instead comprise a series of dot matrix patterns, a series of barcodes or similar or standard Arabic numerals and may comprise a single image per position or multiple repeated images. The encoded images may be printed, marked, indented, etched or similar onto the track 404.

The encoded number sleeve 400 has a helical thread 406 disposed on an inner surface. The number sleeve 400 is threaded to an inner housing part which is fixed relative to the first housing part 104. This threaded connection causes the encoded number sleeve 400 to move axially relative to the first housing part 104 when rotated i.e. when a dose is dialed into or out of the drug delivery device 100. The encoded number sleeve 400 is arranged within the mechanism such that when no dose is dialed into the drug delivery device 100 the first encoded image (encoding position "0") is located directly underneath the recess 114. This allows the encoded image to be viewed by the optical sensor 214. The pitch of the track 404 is the same as the threads on the encoded number sleeve 300 and inner housing such that as the number sleeve 400 rotates and moves axially out of the first housing part 104 the track 404 remains located underneath the recess 114.

The microprocessor 202 is configured to employ software stored in the ROM 204 to determine the content of each image, for example which parts of the image are black and which parts are white, and to identify a corresponding rotational position of the encoded number sleeve 400 relative to the second sensor 214. The microprocessor 202 may achieve this by consulting a table stored in the ROM 204 which relates the content of each image to a rotational position of the number sleeve 400 and hence to a drug dose which has been dialed.

The conductively encoded number sleeve 300 also has an internal thread (not visible in FIG. 5*a*). This thread has the same pitch as the helical tracks 304, 306 such that the tracks 304, 306 are always positioned directly underneath the contacts. The conductively encoded number sleeve 300 is mounted in the drug delivery device 100 in the same way as described above for the optically encoded number sleeve 400 and moves in the same way during dialing and delivery.

The encoded number sleeve 300, 400 is so called because it may replace the traditional "number sleeve" provided in pen type injection devices. The traditional number sleeve has Arabic numerals printed thereon, which are viewed by a user through a transparent window in the housing. The encoded number sleeves 300, 400 described above may have Arabic numerals in addition to the conductive/optically encoded tracks. An additional transparent window may be provided in the first housing part 104 to allow a user to see the numbers. Alternatively, the encoded number sleeves 300, 400 may not have numerals.

Figure 6:
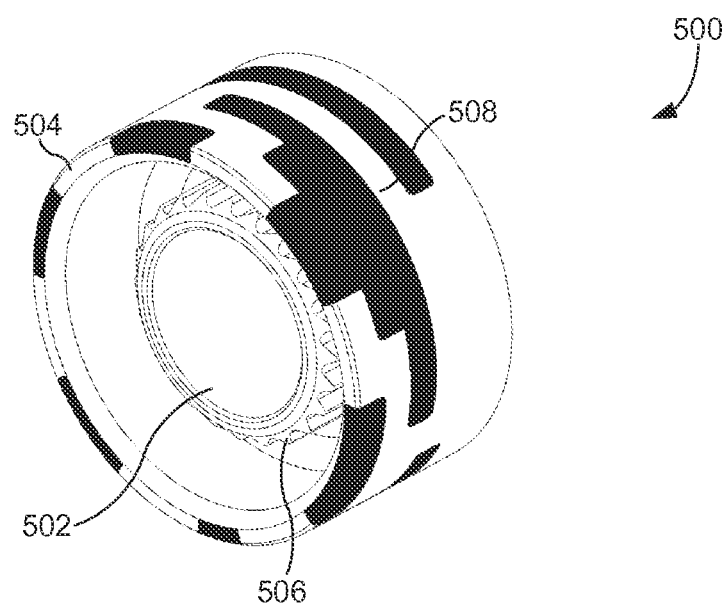
FIG. 6 shows an encoded member forming part of the drug delivery device of FIG. 1.
Figure 7:
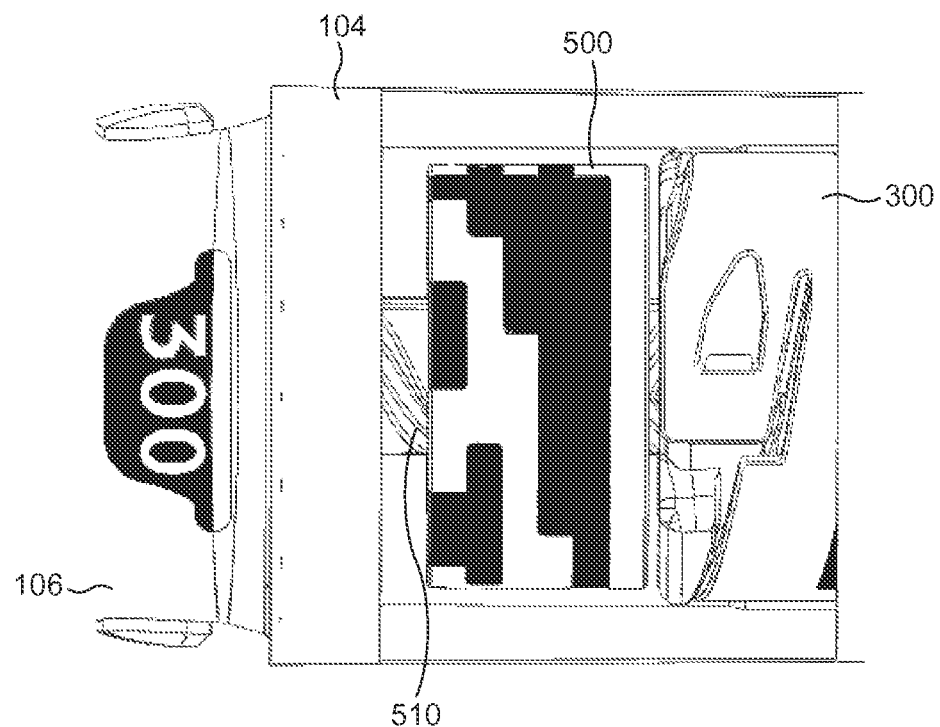
FIG. 7 is a cut away view of a portion of the drug delivery device of FIG. 1 showing the encoded member of FIG. 6 and a portion of the encoded number sleeve of FIG. 5*a*.

Referring now to FIGS. 6 and 7, FIG. 6 shows an example of an encoded member 500 (also referred to as an encoded nut 500 and encoded lead screw nut 500) and FIG. 7 shows the encoded member 500 mounted in the drug delivery device 100. The encoded member 500 is the first rotatable component previously mentioned.

The encoded member 500 is formed of two concentric cylinders, hereafter referred to as the inner section 502 and the outer section 504, joined by a ring of material. The ring of material joining the inner and outer sections 502, 504 may be continuous or alternatively may comprise several partial rings. An inner surface of the inner section 502 of the encoded member 500 has a groove form or thread (not visible in FIG. 6).

An outer surface of the inner section 502 of the encoded member 500 may comprise a number of biasing teeth 506 (as shown in FIG. 6). These teeth may be engaged by one or more biasing elements (not shown) which ensure that there is no rotational float of the encoded member 500 by constraining it to discreet rotational positions. Alternatively, the biasing feature may be omitted and the outer surface of the inner section 502 of the encoded member 500 may be smooth.

The outer surface of the outer section 504 of the member 500 is provided with a number of circular tracks 508 arranged adjacent to one another. In some embodiments, each track 508 comprises conductive and non-conductive segments. In FIG. 6, the conductive segments are shown as white areas and the non-conductive segments are shown as black areas. The member 500 may be made of a metal material such as brass. The member 500 may be machined such that the outer surface has channels and ridges which, when the channels are filled with a non-conductive material, form the tracks 508. In some embodiments, the member 500 has six tracks 508. The tracks 508 may be arranged such that all of the conductive regions are electrically connected.

Referring to FIG. 7, the encoded member 500 is configured to be mounted at the distal end of the first housing part 104. The distal end of the encoded number sleeve 300, 400 is also visible in FIG. 7. A part of the spindle 510 of the drug setting and delivery mechanism is also visible in FIG. 7. The spindle 510 is coupled (via a bearing) to the piston of the drug cartridge. Therefore axial movement of the spindle 510 causes expulsion of the medicament in the drug cartridge. The groove form on the inner surface of the inner section 502 of the encoded member 500 is configured to engage with a thread of the spindle 510. The encoded member 500 is constrained axially within the housing. Therefore, when the spindle 510 is advanced during dispensing of the drug delivery device 100, the encoded member 500 rotates. The spindle 510 does not move when a dose is being dialed into or out of the drug delivery device 100. Therefore, the encoded member 500 does not rotate during dialing.

The encoded member 500 is also suitable for use in drug delivery devices 100 in which the spindle 510 does not rotate during drug dispensing, but only advances axially. In these alternative embodiments, the spindle 510 may comprise one or more protrusions which do not extend over any significant axial distance. These protrusions may engage with the groove form on the inner surface of the inner section 502 of the encoded member 500 and cause the encoded member 500 to rotate as the spindle 510 advances.

Each of the tracks 508 is configured to be engaged by a contact. These contacts together form the first sensor 212. The contacts may be biased against the outer surface of the encoded member 500 in order to provide a stable electrical connection. The encoded member 500 of FIG. 6 has five encoded tracks 508 and a ground track. The ground track ensures that all of the conductive regions are connected together. Therefore, when power is supplied to the ground track (or any other conductive segment), all of the conductive segments are energized. The microprocessor 202 may therefore cause a power signal to be applied to a sixth contact and detect signals from each of the other contacts in order to determine the pattern of conductive and non-conductive segments underneath the contacts at any time.

In some embodiments, each track 508 comprises 24 sections. Therefore, one complete rotation of the encoded member 500 corresponds to a delivered dose of 24 units. Although it is possible that the encoded member 500 could be provided with 7 tracks forming a seven bit encoding system, this is generally not necessary. As the encoded member 500 rotates only during delivery, the absolute amount of the delivered dose can be determined incrementally, even if more than one complete rotation of the encoded member 500 occurs. Alternatively, the conductive and non-conductive segments may be arranged such that a quasi-absolute code is produced i.e. a code in which two rotational positions have the same contact output, but are separated by several positions and can be distinguished incrementally and/or by looking at the previous rotational position.

During dispensing of the device 100, the encoded member 500 rotates as described above. During this process a voltage may be applied to the ground track and signals monitored at the other contacts. In this manner, an amount of medicament which is dispensed may be determined and recorded. It is often necessary for a user of such a drug delivery device 100 to adjust the medicament dose based at least in part on their previous doses. It is therefore advantageous to accurately and automatically record all dispensed doses.

In some other embodiments, the tracks 508 may be optical features printed onto the surface of the encoded member 500. The first sensor 212 may be an optical sensor configured to view and capture images of the surface of the encoded member 500. The microprocessor receives the images form the firsts sensor 212 and determines the amount of rotation of the encoded member 500 and hence the dispensed drug dose.

Having determined the drug dose which has been dispensed, the microprocessor 202 may store the result in the flash memory 205. The display electronics 210 may be controlled to display the result of the dispensed dose determination. The display electronics 210 may display the result of the dispensed dose determination for a predetermined time, for example 60 seconds. Alternatively or in addition, the dispensed dose history may be retrieved electronically from the flash memory 205 by a user of the device 100 or by a health care professional.

Using two different rotatable components and two different sensors to measure the dialed dose and delivered dose offers a level of error checking. The microprocessor 202 is able to monitor the dialed dose (using the encoded number sleeve 300, 400 and second sensor 214) at the start and end of a dose delivery. This information can be compared with the delivered dose as determined using the encoded member 500 and first sensor 212. If there is any discrepancy, an indication of an error may be generated. Also, since the encoded member 500 does not rotate during dialing, the microprocessor 2002 can determine a mode of operation of the device. If the signals received from the first sensor 212 are not changing, the microprocessor 202 can infer that the device 100 is in a dialing mode. If the signals received from the first sensor 212 are changing, the microprocessor 202 can infer that the device 100 is in a delivery/dispensing mode.

The invention is suitable for use in both disposable and re-useable pen type drug delivery devices. In a re-usable device, the drug cartridge may be removed and replaced with a full cartridge. The spindle 510, which has been fully extended in a proximal direction, is screwed or simply pushed back into the device. During this process, the encoded member 500 rotates in the opposite direction to the dispensing direction. The microprocessor 202 may be configured to detect that the encoded member 500 is rotating in the opposite direction and infer that a new cartridge has been attached to the drug delivery device 100.

The invention claimed is:

1. A decoding system for use with a drug delivery device having a drug dose dialing mode and a drug dose delivery mode, the decoding system comprising:
   a first sensor configured to read encoded information from a first rotatable component of a drug delivery device;
   a second sensor configured to read encoded information from a second rotatable component of a drug delivery device, wherein the second sensor comprises an optical sensor configured to be directed at the second rotatable component; and
   a processor configured to:
      receive signals from the first and second sensors;
      determine from the received signals whether the drug delivery device is in a drug dose dialing mode or a drug dose delivery mode.

2. A decoding system according to claim 1, wherein the processor is configured to determine, from signals received from the first sensor, a drug dose that has been delivered.

3. A decoding system according to claim 1, wherein the first sensor comprises an optical sensor configured to be directed at the first rotatable component.

4. A decoding system according claim 3, wherein the outer surface of the first rotatable component is provided with a track comprising a sequence of encoded images and wherein the optical sensor is configured to be directed at the track so as to read the encoded images.

5. A decoding system according to claim 1, wherein the first sensor comprises an array of one or more contacts configured to engage with the first rotatable component.

6. A decoding system according claim 5, wherein an outer surface of the first rotatable component is provided with a plurality of tracks together forming an encoder, each track comprising conductive segments and non-conductive segments, and wherein each track is configured to be engaged by at least one of the one or more contacts.

7. A decoding system according claim 1, wherein an outer surface of the second rotatable component is provided with a track comprising a sequence of encoded images and wherein the optical sensor is configured to be directed at the track so as to read the encoded images.

8. A decoding system according to claim 1, wherein the second sensor comprises an array of one or more contacts configured to engage with the second rotatable component.

9. A decoding system according to claim 8, wherein an outer surface of the second rotatable component is provided with at least one track forming an encoder, each track comprising conductive segments and non-conductive segments, and wherein each track is configured to be engaged by at least one of the one or more contacts.

10. A decoding system according to claim 1, wherein the processor is further configured to determine, from signals received from the second sensor, a drug dose that has been dialed into the drug delivery device.

11. A decoding system according to claim 1, wherein the decoding system is part of a supplementary device configured to be attached to a drug delivery device.

12. A drug delivery device comprising a housing retaining a decoding system comprising:
   a first sensor configured to read encoded information from a first rotatable component of the drug delivery device;
   a second sensor configured to read encoded information from a second rotatable component of the drug delivery device, wherein the second sensor comprises an optical sensor configured to be directed at the second rotatable component; and
   a processor configured to:
      receive signals from the first and second sensors; and
      determine from the received signals whether the drug delivery device is in a drug dose dialing mode or a drug dose delivery mode.

13. A method of using a decoding system comprising:
   receiving a signal from a first sensor configured to read encoded information from a first rotatable component of a drug delivery device;
   receiving a signal from a second sensor configured to read encoded information from a second rotatable component of a drug delivery device; and
   determining that the drug delivery device is in a drug dose dialing mode of operation if there is a change detected in the readings from the second rotatable component and no change detected in the readings from the first rotatable component, or determining that the drug delivery device is in a drug dose delivery mode of operation if there is a change detected in the readings from the first and second rotatable components.

* * * * *